(12) United States Patent
Hatakeyama et al.

(10) Patent No.: US 7,449,691 B2
(45) Date of Patent: Nov. 11, 2008

(54) DETECTING APPARATUS AND DEVICE MANUFACTURING METHOD

(75) Inventors: Masahiro Hatakeyama, Kanagawa (JP); Takeshi Murakami, Tokyo (JP); Tohru Satake, Kanagawa (JP); Nobuharu Noji, Kanagawa (JP); Ichirota Nagahama, Ibaraki (JP); Yuichiro Yamazaki, Tokyo (JP)

(73) Assignees: Ebara Corporation, Tokyo (JP); Kabushiki Kaisha Toshiba, Tokyo (JP)

( * ) Notice: Subject to any disclaimer, the term of this patent is extended or adjusted under 35 U.S.C. 154(b) by 4 days.

(21) Appl. No.: 11/435,128

(22) Filed: May 17, 2006

(65) Prior Publication Data

US 2006/0219909 A1 Oct. 5, 2006

Related U.S. Application Data

(62) Division of application No. 10/237,986, filed on Sep. 10, 2002, now Pat. No. 7,075,072.

(30) Foreign Application Priority Data

Sep. 10, 2001 (JP) ............................. 273432/2001

(51) Int. Cl.
   *G01N 23/00* (2006.01)
(52) U.S. Cl. ..................... 250/310; 250/441.1; 250/397
(58) Field of Classification Search ................. 250/310
   See application file for complete search history.

(56) References Cited

U.S. PATENT DOCUMENTS

| 4,795,977 A | 1/1989 | Frost et al. |
| 5,434,901 A | 7/1995 | Nagai et al. .................... 378/43 |
| 5,808,312 A | 9/1998 | Fukuda .................... 250/492.2 |
| 5,868,664 A * | 2/1999 | Speier et al. ................. 600/112 |
| 6,038,018 A | 3/2000 | Yamazaki et al. |
| 6,067,153 A | 5/2000 | Mizuno |
| 6,184,526 B1 * | 2/2001 | Kohama et al. ............. 250/310 |

(Continued)

FOREIGN PATENT DOCUMENTS

EP 0 452 114 A2 10/1991

(Continued)

OTHER PUBLICATIONS

European Patent Office Communication including European Search Report for corresponding European Patent Application 02020243.8 dated Apr. 10, 2003.

(Continued)

*Primary Examiner*—David A. Vanore
*Assistant Examiner*—Phillip A. Johnston
(74) *Attorney, Agent, or Firm*—Westerman, Hattori, Daniels & Adrian, LLP.

(57) ABSTRACT

A detecting apparatus for detecting a fine geometry on a surface of a sample, wherein an irradiation beam is irradiated against the sample placed in a different environment different from an atmosphere and a secondary radiation emanated from the sample is detected by a sensor, and wherein the sensor is disposed at an inside of the different environment, a processing device to process detection signals from the sensor is disposed at an outside of the different environment, and a transmission means transmits detection signals from the sensor to the processing device.

4 Claims, 10 Drawing Sheets

U.S. PATENT DOCUMENTS 6,465,781 B1 * 10/2002 Nishimura et al. .......... 250/306
6,655,983 B1 12/2003 Ishikawa et al.
6,765,609 B1 * 7/2004 Kinoshita ................ 348/222.1

FOREIGN PATENT DOCUMENTS

JP 2000-113848 4/2000

OTHER PUBLICATIONS

D3 Miroslav Horacek: "Detection of the Angular Distribution of the Signal Electrons in VLESEM" Journal of Computer Assisted Microscopy, vol. 10, No. 1, pp. 23-32.
Communicatin from the European Patent Office dated Apr. 25, 2008 for the corresponding EP APplication No. 02 020 243.8.
Office Action dated Jul. 11, 2008 issued in corresponding Korean application No. 2002-54248.

* cited by examiner (j=4000  i=500)

DETECTING APPARATUS AND DEVICE MANUFACTURING METHOD

RELATED APPLICATION

This application is a divisional of U.S. patent application Ser. No. 10/237,986 filed on Sep. 10, 2002 now U.S. Pat. No. 7,075,072, which is incorporated by reference in its entirety. Priority under 35 U.S.C. 120 and 121 is hereby claimed for benefit of the filing date of U.S. patent application Ser. No. 10/237,986.

BACKGROUND OF THE INVENTION

The present invention relates to a detecting apparatus for detecting a fine geometry (an image) on a surface of a sample by irradiating an irradiation beam against the sample and then detecting and processing a secondary radiation emanated from the sample. The fine geometry on the surface of the sample, for the purpose of the present invention, includes a defect in such a high density pattern having a minimum line width of 0.15 μm or smaller formed on a wafer surface of a semiconductor device, for example. The present invention also relates to a manufacturing method of a semiconductor device employing such a detecting apparatus.

There has been known such a detecting apparatus which comprises an electron gun for emitting an electron beam into a vacuum chamber, an illuminating optical system consisting of a series of electrostatic lenses, a stage for carrying a wafer to be inspected, a map projecting optical system consisting of a series of electrostatic lenses, and a sensor. This known detecting apparatus further comprises an MCP (Micro Channel Plate) for amplifying detected electrons, a fluorescent screen for converting the amplified electrons into a light, an FOP (Fiber Optic Plate) functioning as a relay between a vacuum system within a vacuum chamber and an external component for transmitting the optical image converted by the fluorescent screen, and an image-taking device such as a CCD (Charge Coupled Device) for capturing an optical image output from the FOP, wherein the vacuum system within the vacuum chamber is hermetically sealed against an external environment but an electric signal can be transmitted from the inside of the vacuum chamber to the outside thereof.

FIG. 1 and FIG. 2 show schematic diagrams illustrating prior art detecting apparatuses. A detecting apparatus of FIG. 1 comprises a vacuum vessel 20 for accommodating a sample 10, or a semiconductor wafer, for example, a hermetic glass plate 21 transparent to the light emitted from the sample, a lens 31 disposed in the atmosphere, a sensor 32, and a camera 33. An image signal for the sample generated in the sensor 32 is input to the camera 33 and converted into image data. The image data is used in a defect inspection for the sample by a comparative method among dies, that is, a method in which the comparison is applied among pattern images obtained from the corresponding regions (observational screens) of the dies (chips) aligned on different wafers (see JP-A-5-258703, JP-A-6-188294).

A detecting apparatus 2 shown in FIG. 2 is similar to the detecting apparatus of FIG. 1 with the exception that a sample 10 of FIG. 2 emanates secondary electrons 11, which in turn are converted into a light by a fluorescent screen 19. Specifically, in the detecting apparatus of FIG. 2, the secondary electrons 11 emanated from the sample 10 by irradiating a primary electron beam against the sample 10 are introduced into the fluorescent screen 19 via an electronic optical system having a lens 12 and an amplifier 13, and then the electrons 11 are converted into the light by the fluorescent screen 19. The light from the fluorescent screen 19 is guided out of a vacuum vessel 20 through a hermetic glass plate 21 and passes through a lens 31 to be introduced into a sensor 32. The sensor 32 generates an image signal for the sample, which in turn, is input to the camera 33 to be converted into image data.

However, the prior art detecting apparatus shown in FIG. 1 and FIG. 2 has such a drawback that the intensity of the light reaching the sensor has been attenuated since in this apparatus the light beam passes through the hermetic glass plate defining the inside and outside of the vacuum vessel and also through the lens and then enters the sensor in the atmosphere so as to be converted into the image signals for the sample surface. The attenuation factor of this configuration is observed to be, for example, in the range of $1/20$ to $1/2$. In addition to the problem of the attenuation occurring in the intensity of the light, the prior art detecting apparatus also has another problem that the hermetic glass plate and/or the lens may cause an aberration or distortion in the light beam, inhibiting the capturing of highly accurate image. Furthermore, the prior art apparatus still has another problem that use of many optical components and supporting and/or fixing parts thereof in the apparatus might sometimes cause a mechanical offset among the sensor, the hermetic glass and the lens, which also inhibit the capturing of highly accurate image.

Further, the apparatus shown in FIG. 2 using the conventional electronic optical system, in which the image information represented by the electrons is converted into light and then thus converted light is in turn detected, is also problematic in that the efficiency and resolution may deteriorate as a result of this conversion. An object of the present invention is to provide a detecting apparatus which provides a solution to the problems pertaining to the apparatuses according to the prior art. In specific, the object of the present invention is to improve a resolution and a throughput of inspection of a detecting apparatus for detecting a fine geometry (an image) on a surface of a sample by, in an environment different from that of the atmosphere, irradiating an irradiation beam against the sample and then detecting and processing a secondary radiation emanated from the sample. These and other objects of the present invention will be apparent from the description described below.

SUMMARY OF THE INVENTION

According to the present invention, a detecting apparatus for detecting a fine geometry on a surface of a sample comprises a means for irradiating an irradiation beam such as an electron beam against a sample placed inside of a different environment different from the atmosphere; a sensor for detecting secondary radiation emanated from the sample and outputting a detection signal containing information of the sample surface; a processing device for processing the detection signal; and a transmission means for transmitting the detection signal from the sensor to the processing device. In the detecting apparatus of the present invention, the sensor is disposed at an inside of the different environment, the processing device is disposed at an outside of the different environment, and the transmission means is designed so as to penetrate through a flange structure which separates the inside of the different environment from the outside thereof. In this case, it is possible to use a sensor package which is constituted so as to include the sensor and the transmission means. The wires or pins of the sensor package in the inside of the different environment are connected to connecting sockets of pins of the processing device through pins of a feed through formed in the flange structure.

A feed through has generally a structure wherein conductive pins penetrate a plate member made of a insulating material, and has an ability to transmit different signals by including a plurality of pins. A feed through also has a seal property and can be used at a place to separate the inside from the outside of a different environment. The feed through is connected to a place of a flange structure by welding or by using an O-ring. The way for attaching a feed through to a vacuum vessel is not limited to a flange structure shown in FIG. 4 but is able to include a fitting-in structure shown in FIG. 3.

The irradiation beam is a beam selected from a group consisting of an electron beam, an X-ray, an X-ray laser, an ultraviolet ray and an ultraviolet-ray laser. Further, the secondary radiation beam is one selected from a group consisting of secondary electrons, back scattered electrons, reflected electrons, photoelectrons and scattered lights (reflected lights). A pressure and a gas species inside of the different environment may be different from those of the outside thereof, which means that, for example, the inside of the different environment is defined as a vacuum and the outside of the different environment is defined as an atmosphere.

For the flange structure and the feed through, the aforementioned one can be used. In order to improve signal transmission performance, a sensor package which integrates a sensor and signal transmission pins can be used. The sensor package has a function of a table for securing and wiring of the sensor. Wirings may be formed between a pad electrode on the surface of the sensor and a pad of the package by using bonder or the like. By using a sensor package with function of feed through, the wiring distance is reduced, and it is possible to improve transmission signal frequency property (e.g. by 20-30%) and to decrease noise (e.g. by 20-30%) of signals.

A detecting apparatus for detecting a surface geometry of a wafer according to the present invention comprises an electron beam irradiation means for irradiating an electron beam against the wafer, a sensor for detecting secondary radiation beam emanated from the wafer and then outputting a detection signal containing information of the wafer surface, an electronic control means for directing the secondary radiation beam emanating from the wafer onto the sensor, a processing device for processing the detection signal output from the sensor, a vacuum chamber for accommodating the wafer and the sensor, and a transmission means for transmitting the detection signal from the sensor to the processing device. The transmission means extends through the flange structure separating the inside of the different environment from the outside thereof. The electronic control means may include a mapping optical system comprising, for example, a noise-cut aperture (an aperture provided to cut electrons or a light which could be a noise factor such as stray electrons) and an electronic amplifier.

When a sensor, especially such a sensor having a large number of pins and extensive wiring (for example, 100 or more) and is driven at a high rate, is installed in a vacuum environment, some problems occur, including possible deterioration of a signal transmission due to the longer wiring, possible deterioration of a S/N ratio (detection sensitivity) because of a raised operation temperature due to bad heat radiation property in the vacuum environment, and possible damage to the sensor/package due to a greater positioning pressure applied to those pins connecting the sensor/package to a feed through. Such problems could be solved by installing the sensor on an inner surface of the feed through section and making respective socket contacts corresponding to respective pins to include elastic members.

A detecting apparatus of the present invention comprises within a vacuum chamber, a mechanism for irradiating the secondary electrons or a reflected light emitted from the wafer, against the sensor, thereby eliminating the need for the optical lens, the FOP, the hermetic glass plate or fittings for them, so that advantageously, the number of components included in the detecting apparatus can be reduced, the accuracy of position and resolution can be improved, the possible deterioration of optical properties in transmission to the sensor can be dissolved, and the apparatus can be manufactured at a lower cost.

In the detecting apparatus of the present invention, an entrance plane of the sensor may be coated with an anti-reflection film for preventing reflection of incident electrons. Other than the application of the anti-reflection film, a light-accepting element may be treated such that an electron permeable insulation film is disposed on a surface thereof and a conductive anti-reflection film is coated over the insulation film. For example, a film made of platinum and/or titanium oxide may be used to form the anti-reflection film. Further, the detecting apparatus of the present invention is not limited to the applications in different environments such as the vacuum as stated above, but for image detection, the detecting apparatus may be placed, for example, in other environments containing species of gas different from those in the atmosphere or in the water, so far as the environment allows the light or electrons to be transmitted therein.

An electron beam, an ultraviolet ray (an ultraviolet light), a far ultraviolet ray (a DUV ray: an ultraviolet ray having a wave length in the vacuum ultraviolet ray region of 200 to 10 nm), or a laser beam may be used as the irradiation beam. When the electron beam is used, the reflected electrons, the back scattered electrons or the secondary electrons emanated from the sample are used for image detection. Here, the reflected electrons have almost the same energy with the incident electron. When the ultraviolet ray, the DUV ray or the laser beam is used, the photoelectrons is used for the image detection, in which the scattered light generated upon irradiation of such ray or beam onto the sample surface is detected and thus any defects on the sample surface can be detected. The ray or beam may be introduced onto the sample surface or from the sample surface into the sensor in an efficient manner by using a quartz fiber or a hollow fiber.

Advantageously, any combinations of the electron beam with the ultraviolet ray, the far ultraviolet ray or the laser beam may be used as the irradiation beam to be irradiated against the sample surface. When the electron beam is solely used for irradiation, in some cases, the potential on the sample surface may be changed due to the charge-up, inhibiting the uniform irradiation of the electron beam, but in contrast, the use of the ray or beam such as the ultraviolet ray, the far ultraviolet ray or the laser beam, which can be irradiated onto the sample surface irrespective of the potential thereon, in combination with the electron beam may help obtain the electrons stably and efficiently from the sample surface, which will be used for image acquisition. For example, if the ultraviolet ray is irradiated, not only are the photoelectrons generated but there is also a formation of a lot of electrons excited into a metastable state, and in this condition, if the primary electron beam is additionally irradiated, the number of free electrons is increased, stimulating the emission of the secondary electrons in an efficient manner. The present invention further discloses a manufacturing method of a semiconductor device including an inspection process for inspecting a wafer for any defects in the course of processing, using the detecting apparatus as discussed above.

Figure 1:
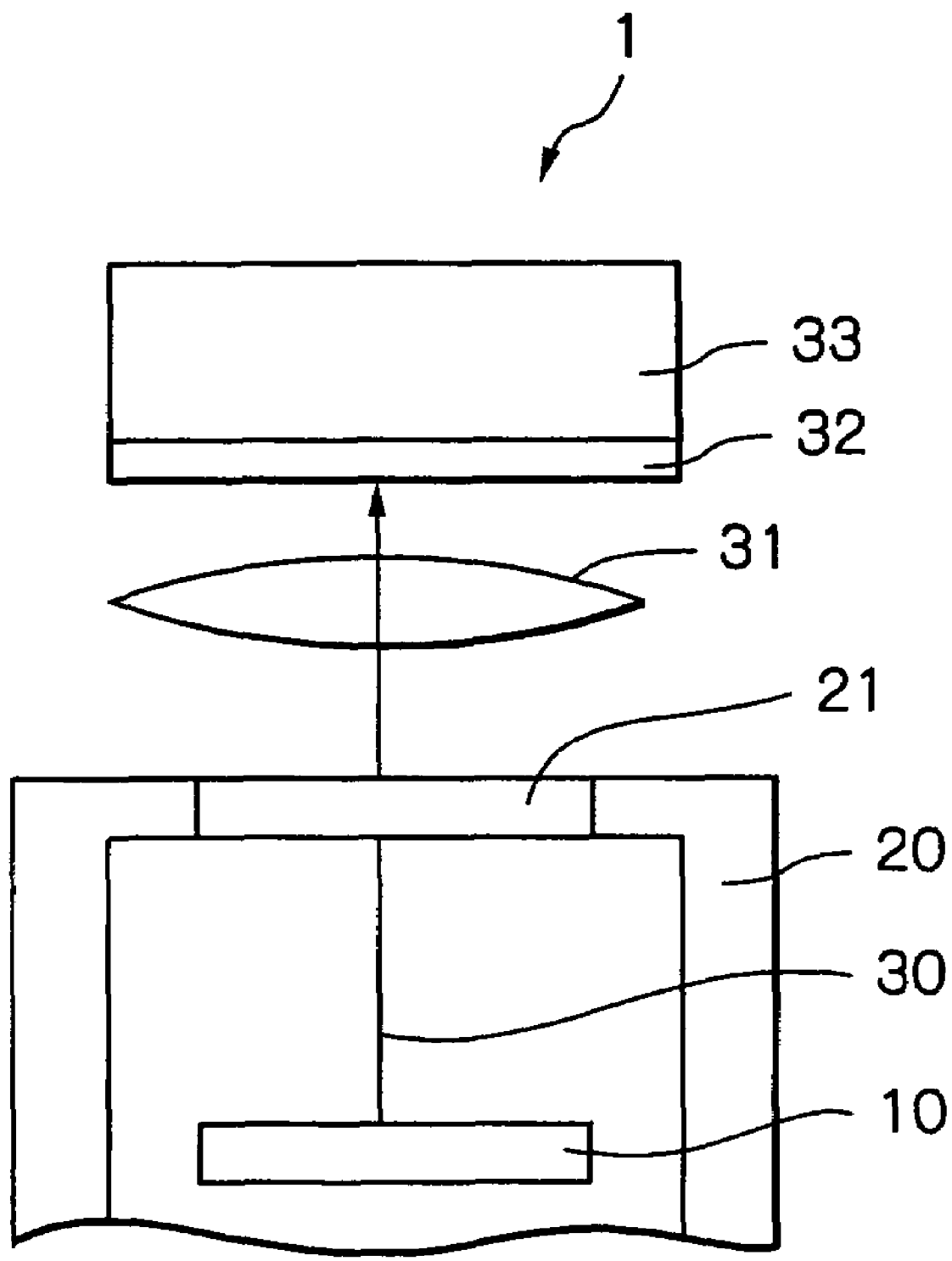
FIG. 1 is a schematic diagram of a detecting apparatus according to the prior art.

wherein, reference numerals 1-8 are detecting apparatus; 9 is an x y z θ stage; 10 is a sample; 11 is a secondary radiation; 12 is an electronic optical lens; 13 is an electronic amplifier; 14 is an orbit of electrons; 15 is an electrostatic lens; 16/17 are lenses; 18 is an electronic optical system; 19 is a fluorescent screen; 20 is a vacuum vessel; 21 is a hermetic glass; 22 is a feed through; 30 is a light; 31 is a lens; 32 is a sensor; 33 is a camera; 43 is an ultraviolet ray; 44 is a fiber; 45 is a primary electron beam; 46 is a laser; 47 is an E×B filter; 49 is an optical axis; 53 is a wafer processing process; 56 is chip testing process; 61 is a mask manufacturing process; 63 is a lithography process; 76 is a micro channel plate; 77 is a fluorescent section; 78 is a relay optical system; 79 is a TDI sensor; 80 is an image display section; 81 is an electron gun; 82 is an electron beam; 83/84 are lenses; 85 is an E×B filter; 86 is an electrode; 87 is a magnet; 88/89 are lenses; 91 is a sensor surface; and 94 is a magnet lens.

DETAILED DESCRIPTION OF THE INVENTION

Figure 2:
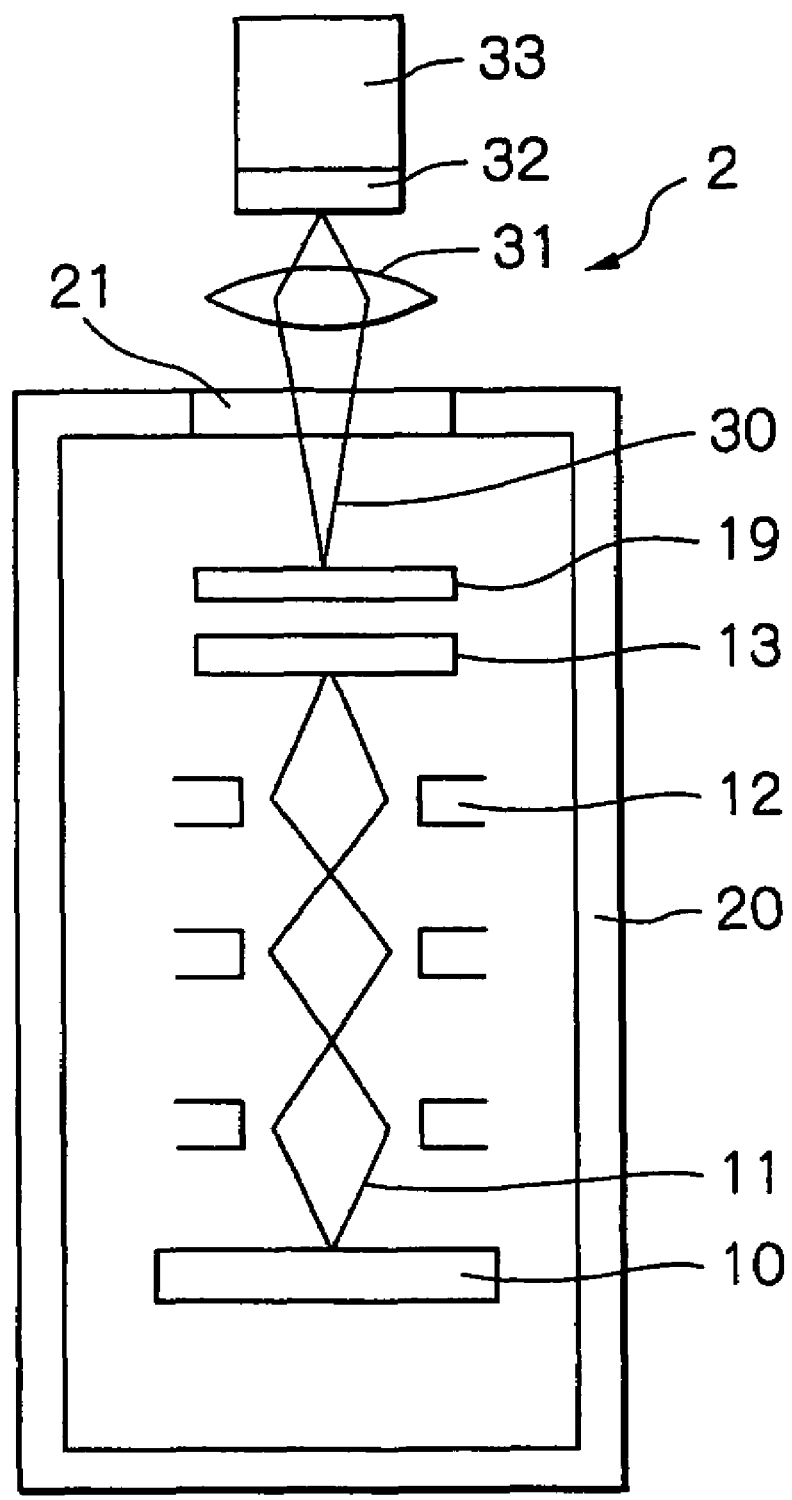
FIG. 2 is a schematic diagram of another detecting apparatus according to the prior art.
Figure 3:
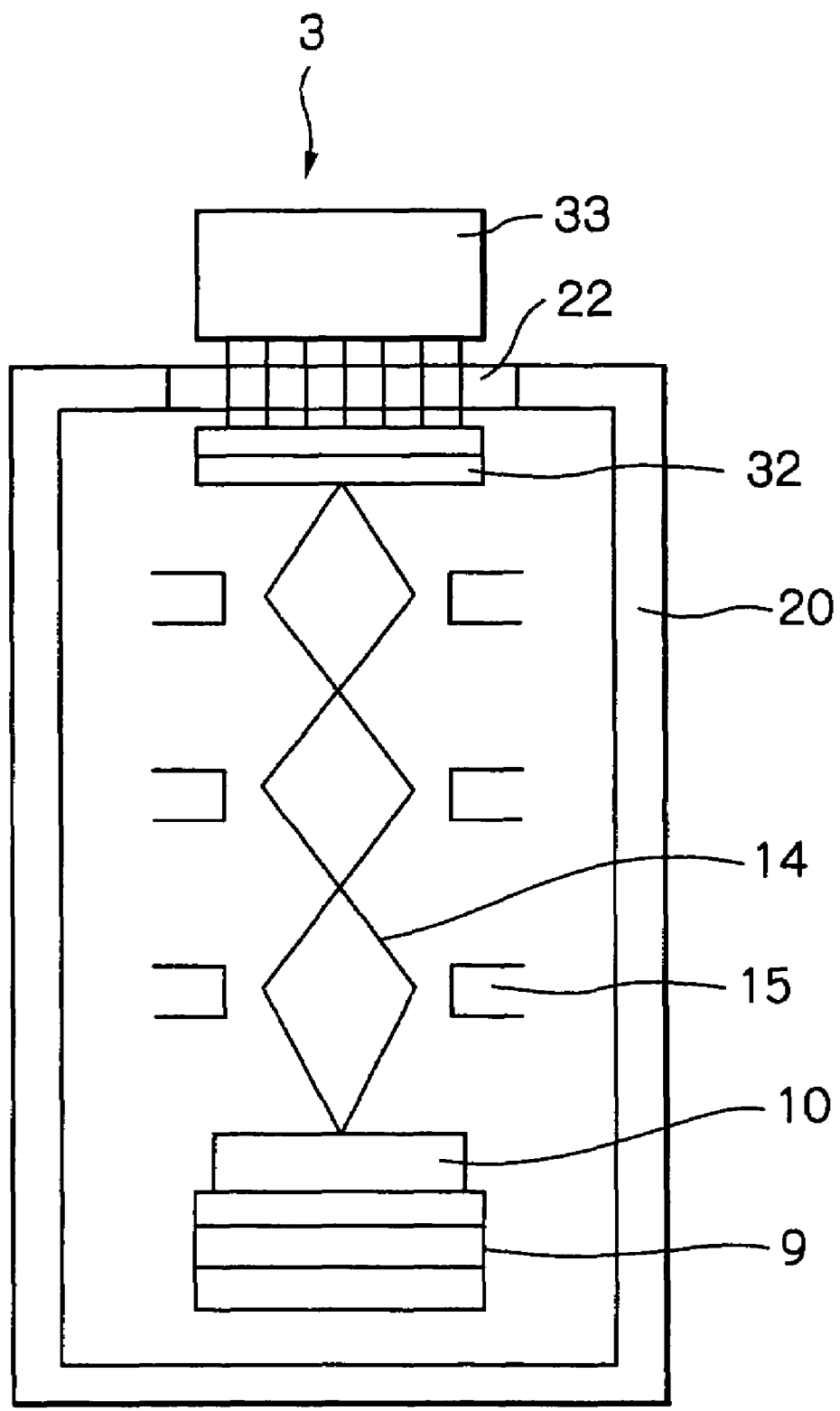
FIG. 3 is a schematic diagram of a detecting apparatus 3 of an embodiment according to the present invention.

FIG. 3 through FIG. 8 show schematic diagrams of detecting apparatuses according to respective embodiments of the present invention, in which some elements corresponding to those of the detecting apparatuses shown in FIG. 1 and FIG. 2 are designated with the same reference numerals and the duplicated descriptions will be omitted. FIG. 3 is a schematic diagram of a detecting apparatus 3 containing a mapping optical system according to an embodiment of the present invention, in which a sensor 32 comprising an EB-CCD (Electron Beam detecting Charge Coupled Device) is disposed within a vacuum vessel 20. Components including a lens of an electronic optical system (an electrostatic lens) 15, an aperture, a stigmatic element (an element for generating an appropriate distribution of an electric field to compensate for astigmatism or spherical aberration) are disposed within the vacuum vessel 20. A sample 10 is a silicon wafer having a diameter of 300 mm and fixedly mounted on a stage 9 by an electrostatic chuck (not shown). The stage 9 is movable in the x-, y- and z-directions and also rotationally (θ) movable.

In the detecting apparatus 3 of FIG. 3, a detection of an image is accomplished by moving the stage 9 so as to detect a predetermined location on the sample 10, and then executing a detecting operation of the location with an appropriate field of view corresponding to a scaling factor at that place for detection, for example, an area of 200×200 μm by using the scaling factor of 300. To execute the detecting operation for a plurality of locations on the sample 10, a series of the above-mentioned operations should be carried out repeatedly at high speed. An electronic signal generated by the sensor 32 consisting of the CCD disposed in the vacuum vessel 20 is drawn out of the vacuum vessel 20 via a feed through 22 so as to be input to a camera 33. Comparisons among images may be carried out by moving the areas subject to comparison into the place for detection to capture the images thereof repeatedly and applying comparisons among obtained data.

Figure 4:
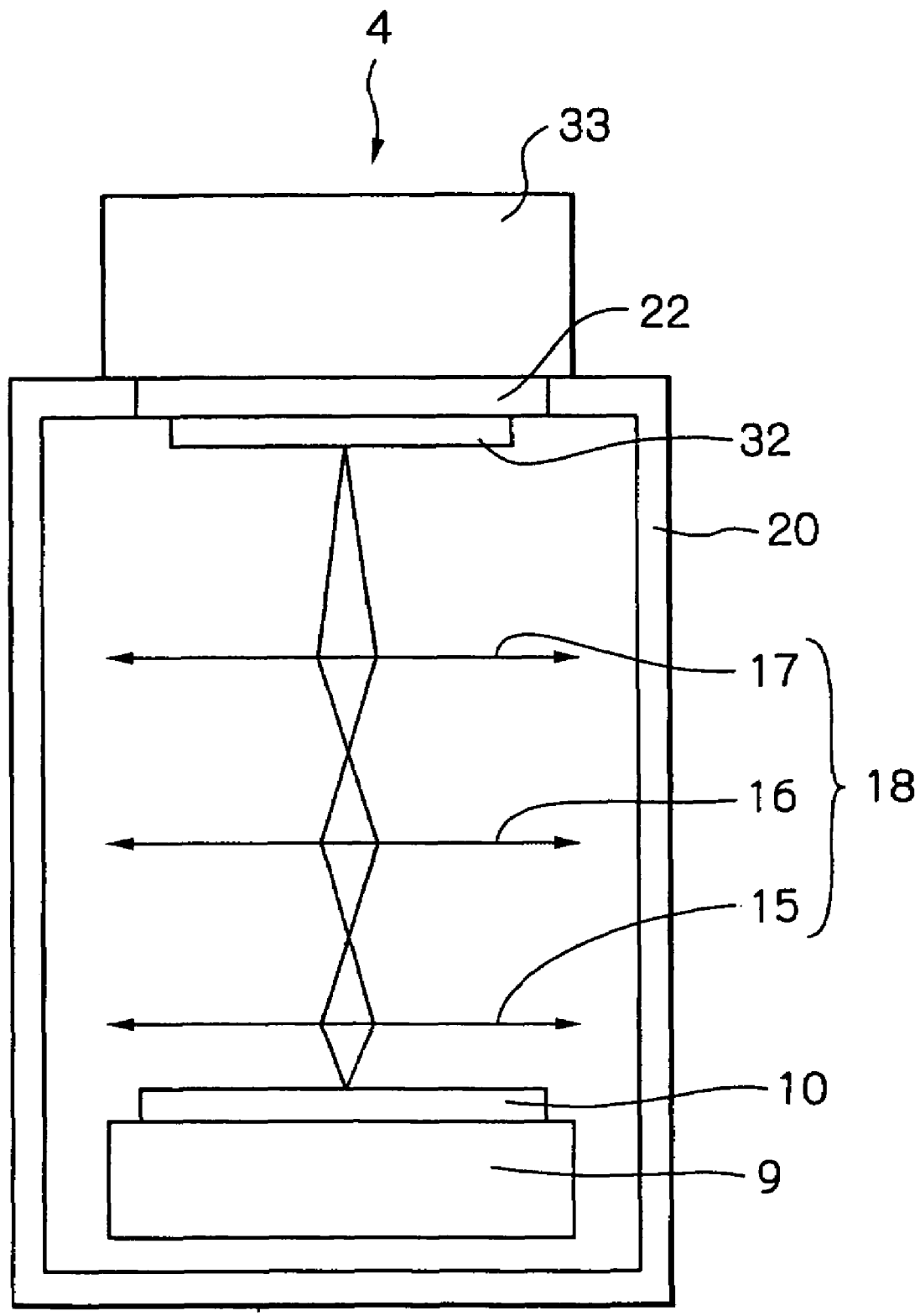
FIG. 4 is a schematic diagram of a detecting apparatus 4 of another embodiment of the present invention.

FIG. 4 is a schematic diagram of a detecting apparatus 4 containing a mapping optical system according to another embodiment of the present invention. A sensor 32 is an EB-TDI (Electron Beam detecting Time Delay and Integration) sensor and the sensor 32 allows the electrons to enter the sensor surface directly in a vacuum environment. The TDI sensor is representative of such a CCD sensor having a sensor structure and function for achieving a TDI (Time Delay and Integration) driving, which integrates the signals by TDI driving during line scanning thus to enable an image taking in a serial moving mode with a high sensitivity and a high signal volume. It should be noted that the structure and circuitry of the TDI sensor are widely different from those in the typical CCD so as to enable the TDI driving. The TDI sensor can form a two-dimensional image by capturing the optical signals. In this specification, the EB-TDI sensor 32 is referred to as such a TDI sensor that permits the electrons to enter the TDI sensor directly and accumulates and integrates the charges thus to form the two-dimensional image.

The EB-TDI sensor 32 may be installed in a package, and the package forms a feed through 22. A pin of the package is directly connected to a camera 33 in the atmosphere side. An electronic optical system 18 may provide the two-dimensional information of a surface of a sample 10 such as a wafer in a scale factor of about 50 to 500 through three-step of lenses 15, 16 and 17. This means that the electronic optical system 18 magnifies the electron beam exited from the two-dimensional area and irradiates thus magnified electron beam directly onto the EB-TDI sensor 32. If the EB-TDI sensor 32 is used, the wafer 10 mounted on the stage 9 (movable in the x-, y- and θ- direction, for example) is serially moved in the direction for integration on the sensor surface (the direction indicated by the arrow S in FIGS. 11 and 12) of the EB-TDI sensor 32, so that the electrons emanated from the wafer surface can enter the EB-TDI sensor 32 through an electronic optical system of map projection type and so on. The electrons multiplied by the integration steps are made to enter the EB-TDI sensor to form the two-dimensional image. The detecting apparatus 4 of FIG. 4 can eliminate those drawbacks, including an optical conversion loss, an aberration/distortion due to an optical transmission, and associatively occurring deterioration in an image resolution, a failure in detection, a high cost and an enlarged profile of the apparatus, pertaining to the conventional detecting apparatus.

If the pixel number of 4000×500 of the EB-TDI sensor is used in the detecting apparatus 4 of FIG. 4, the line pixel information from 4000 lines is integrated serially with 500 steps, as the stage 9 moves, so that a sensor charge intensity responsive to each pixel of the sample can be accumulated sufficiently. When the detecting apparatus 4 of FIG. 4 is applied to a silicon wafer and a pattern structure formed on the surface thereof in the course of a semiconductor circuit manufacturing process as an object for detecting operation, the electron beam or other irradiation beam may be irradiated onto the subject to determine the presence of a defective event such as dusts, a bad conduction, a bad pattern or a lack of pattern, and also to make a state judgment and a sort categorization. In the conventional detecting apparatus using a hermetic glass, an FOP (Fiber Optic Plate) and a lens, there will occur an offset in the pixel on the sensor subject to the integration due to the distortion and/or aberration caused by those components, so that highly accurate image detection cannot be expected. The detecting apparatus 4 of FIG. 4 can achieve a high resolution, a high processing rate, a lower profile, and at a low cost.

Figure 5:
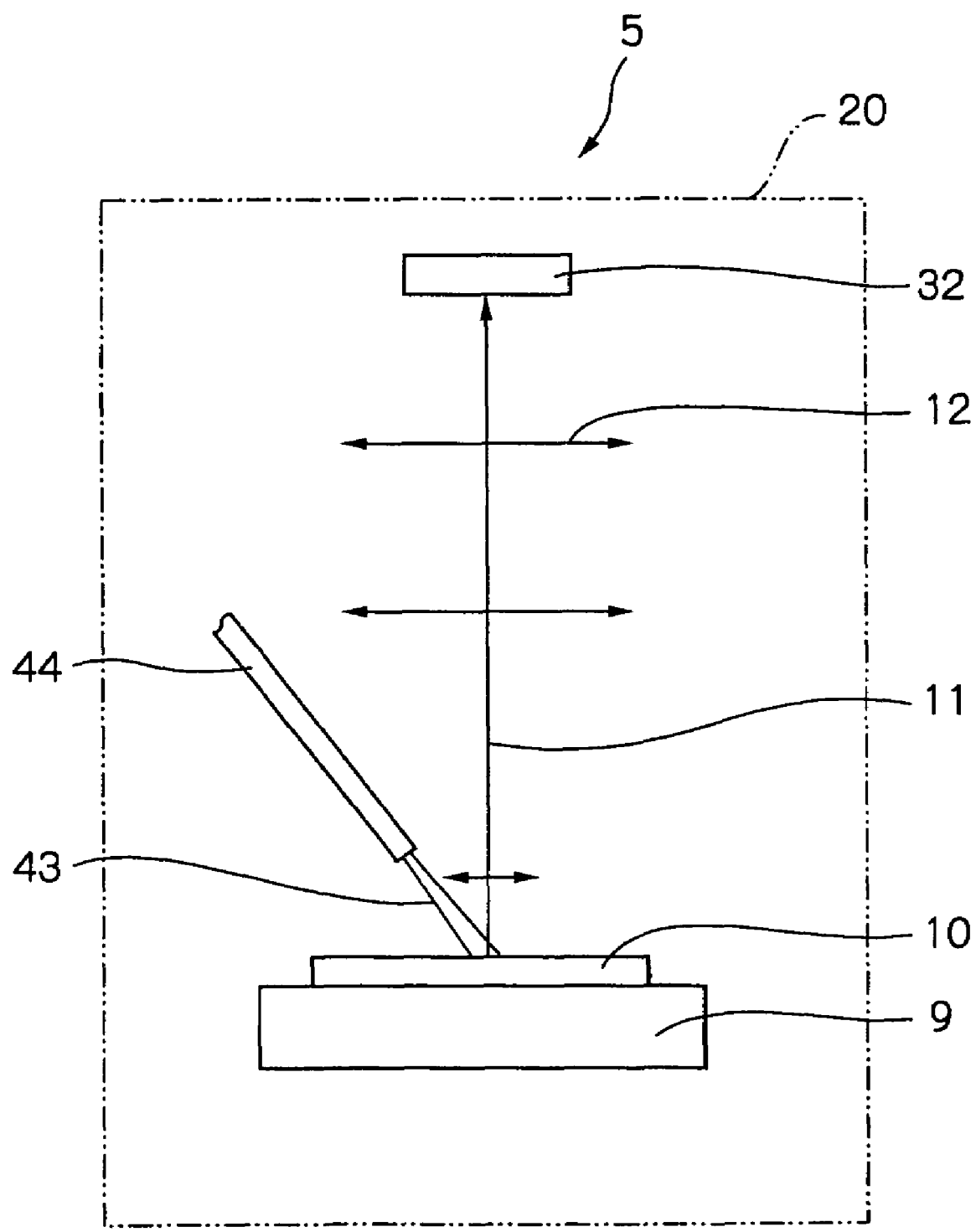
FIG. 5 is a schematic diagram of a detecting apparatus 5 of yet another embodiment of the present invention.

FIG. 5 is a schematic diagram of a detecting apparatus 5 according to another embodiment of the present invention. In the detecting apparatus 5, an ultraviolet ray 43 selected as the primary beam is directed onto a surface of a sample 10, and photoelectrons emanated from the incident points on the surface are guided through a lens, an aperture, a stigmatic element and so on included in an electronic optical system 12 so as to enlarge an electronic image, which is in turn made to enter a sensor 32. The sensor 32 comprises an EB-CCD sensor or an EB-TDI sensor. The ultraviolet ray 43 or the primary beam is transmitted through a hollow fiber 44 and irradiated to a field of view surrounding the center axis of the electronic optical system, for example, an area defined with a diameter of 300 μm.

Figure 6:
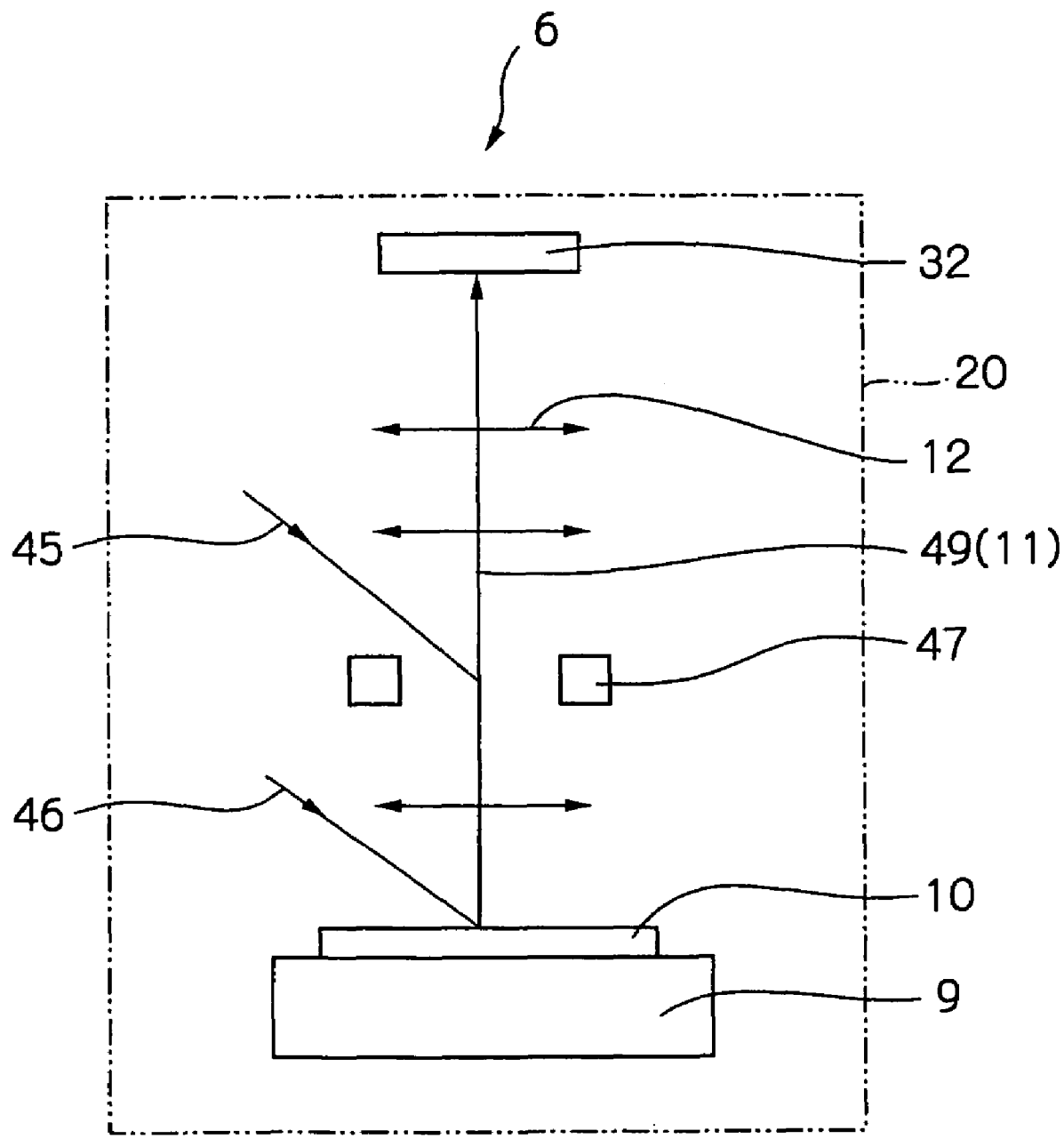
FIG. 6 is a schematic diagram of a detecting apparatus 6 of yet another embodiment of the present invention.

FIG. 6 is a schematic diagram of a detecting apparatus 6 according to another embodiment of the present invention. The detecting apparatus 6 uses a combination of an electron beam 45 and a laser beam 46 as the primary beam. A direction of the electron beam 45 is changed by an E×B filter 47 so as to be aligned with an optical axis 49 of an electronic optical system for detection, and then the electron beam 45 enters a sample 10. A secondary electron beam 11 emanated from the sample 10 goes straight through the E×B filter 47 and is introduced into a sensor 32. The sensor 32 is composed of the EB-TDI sensor. The laser beam 46 may be a quadruple wave of the YAG or an excimer laser. The excimer laser may be introduced through a hollow fiber.

Figure 7:
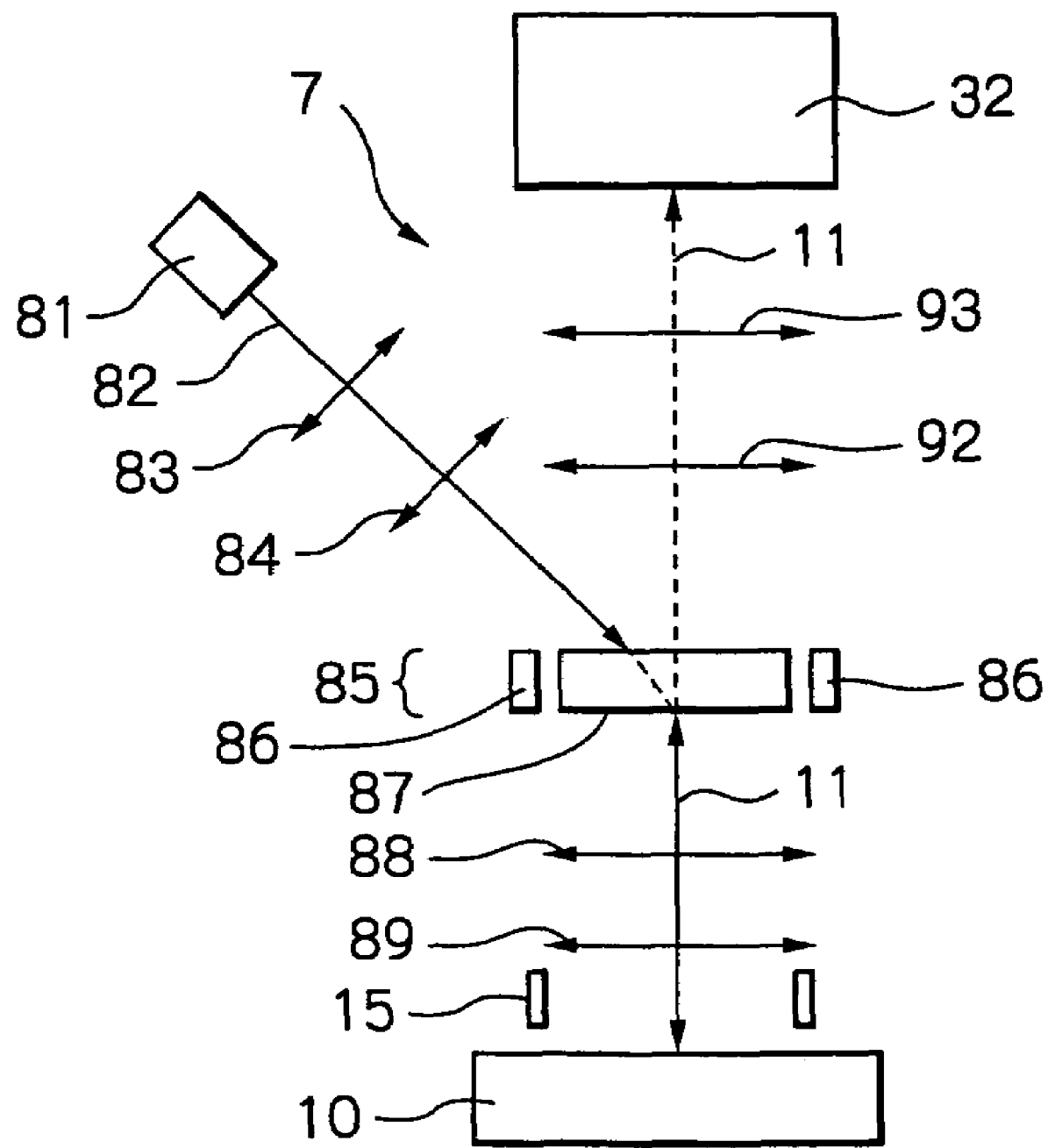
FIG. 7 is a schematic diagram of a detecting apparatus 7 of yet another embodiment of the present invention.

FIG. 7 is a schematic diagram of a detecting apparatus 7 according to another embodiment of the present invention. The detecting apparatus 7 is an electron beam detecting apparatus of map projection type, in which an electron beam 82 emitted from an electron gun 81 is shaped through a square opening, contracted by a two-step of lenses 83, 84, and focused onto a central area on a deflecting plane of an E×B filter 85, forming a square image having each side of 1.25 mm. Thus shaped beam, which has been deflected by the E×B filter 85, is then contracted into a scale of ⅕ by lenses 88, 89 and projected on a sample 10. Secondary electrons emanated from the sample, which contain information of a pattern image, are enlarged through a four-step of lenses 89, 88, 92 and 93, and made to enter a sensor 32.

The lens 89 in combination with the lens 88 forms a symmetric tablet lens, while the lens 92 in combination with the lens 93 forms another symmetric tablet lens, meaning that the series of lenses 89, 88, 92 and 93 together form a non-distortion lens set. However, since any dust on an electrode may somehow cause a distortion, it is suggested that a reference pattern should be regularly placed on the surface of the sample to measure any distortions, so that parameters to be used to compensate for the distortions could be calculated beforehand.

On one hand, if the sample is such a wafer that an oxide film or a nitride film may be selectively formed thereon, only making a correction to the optical distortion is not sufficient, but in this case, another step of correction to the distortion should be added upon acquisition of the image data by selecting representative points from the edge portion of the pattern and comparing those points to the image of the data. Subsequently, a die-to-die comparison, or a comparison between images of the patterns obtained from the same regions (the observational screens) of dies (chips) arranged on different wafers, or another comparison between plural sets of image data may be applied to detect any defects. Since in the detecting apparatus of the present invention, the EB-CCD sensor or the EB-TDI sensor, to which the electrons are irradiated directly to make an image detection, is installed in the vacuum environment, the image acquisition can be accomplished with high contrast and high resolution and also a higher throughput without any optical transmission loss can be achieved at a lower cost as compared to the detecting apparatuses according to the prior art.

When Secondary Radiation is Composed of Secondary Electrons

In the embodiment of FIG. 7, if the secondary radiation is composed of secondary electrons, the electron beam to be irradiated onto the wafer is prepared so as to have, for example, a beam energy within the range of 10 to 4000 eV, and an elliptical beam profile with a radius "a" of 250 μm and a radius "b" of 100 μm, and irradiated onto the wafer surface approximately perpendicularly thereto. A current density should be set to be within the range of $1\times10^{-5}$ to $1\times10^{-1}$ A/cm$^2$. An amount of emission of the secondary electrons depends on the current density of the irradiated electron beam or the total current value thereof. When an emission ratio of the secondary electrons is 1, the same amount of secondary electrons as that of the incident electrons may be emanated. Energy of the secondary electrons is typically within the range of 0 to several eV.

When a scale factor of a sample surface to a sensor surface of the mapping optical system is assumed to be 200, and if the field of view on the wafer (visual field) is 200 μm×50 μm, a corresponding area on the sensor surface should be 40 mm×10 mm. When the current value irradiated within the 200 μm×50 μm field of view is 2 μA and the emission ratio is 1, the amount of emanated secondary electrons is 2 μA. The emanated secondary electrons pass through the objective lenses 88 and 89, and then pass the E×B filter 85 under a rectilinear propagation condition. Subsequently, the beam of the secondary electrons is enlarged by the lens 92, NA aperture (not shown) and the lens 93, and then enters the sensor surface.

The NA aperture (not shown) functions to limit a transmittance and an aberration. When the transmittance is 3%, a current of 2 μA×0.03=60 nA enters the sensor surface. The EB-TDI sensor or the EB-CCD sensor is used as the sensor. When the EB-TDI sensor is employed, 2-dimensional image can be obtained while moving continuously. The wafer mounted on the stage movable in x-, y-, θ- and z-directions is continuously moved along a direction corresponding to the integrating direction of the sensor so as to integrate the charges of the EB-TDI sensor and to obtain the image. In the EB-TDI sensor, for example, the pixel size is 20 μm×20 μm, the pixel number is 2000×500, and 500 steps of pixels are arranged in the integrating direction.

When Secondary Radiation is Composed of Reflected Electrons

In the embodiment of FIG. 7, if the secondary radiation is composed of reflected electrons, the electron beam to be irradiated onto the wafer is prepared so as to have, for example, a beam energy within the range of 10 to 4000 eV, and an elliptical beam profile with a radius "a" of 250 μm and a radius "b" of 100 μm, and irradiated onto the wafer surface approximately perpendicularly thereto. A current density should be set to be within the range of $1 \times 10^{-3}$ to $5 \times 10^{-1}$ A/cm². An amount of emission of the reflected electrons depends on the current density of the irradiated electron beam or the total current value thereof. The electrons emanated from the sample surface with the same energy as of the incident electron beam are treated as the reflected electrons. The emission ratio of the reflected electrons is lower than that of the secondary electrons and is typically less than 1/10.

When a scale factor of the sample surface to the sensor surface of the mapping optical system is assumed to be 200, and if the field of view on the wafer (visual field) is 200 μm×50 μm, a corresponding area on the sensor surface should be 40 mm×10 mm. When the current value irradiated within the 200 μm×50 μm field of view is 2 μA and the emission ratio is 0.1, the amount of emanated reflected electrons is 0.2 μA. The emanated reflected electrons pass through the objective lenses 88 and 89, and then pass the E×B filter 85 under a rectilinear propagation condition. Subsequently, the beam of the reflected electrons is enlarged by the lens 92, NA aperture (not shown) and the lens 93, and then enters the sensor surface.

The NA aperture (not shown) functions to limit a transmittance and an aberration. When the transmittance is 10%, a current of 2 μA×0.1=20 nA enters the sensor surface. The EB-TDI sensor or the EB-CCD sensor is used as the sensor. When the EB-TDI sensor is employed, 2-dimensional image can be obtained while moving continuously. The wafer mounted on the stage movable in x, y, θ and z directions is continuously moved along a direction corresponding to the integrating direction of the sensor so as to integrate the charges of the EB-TDI sensor and to obtain the image. In the EB-TDI sensor, for example, the pixel size is 20 μm×20 μm, the pixel number is 2000×500, and 500 steps of pixels are arranged in the integrating direction.

Figure 8:
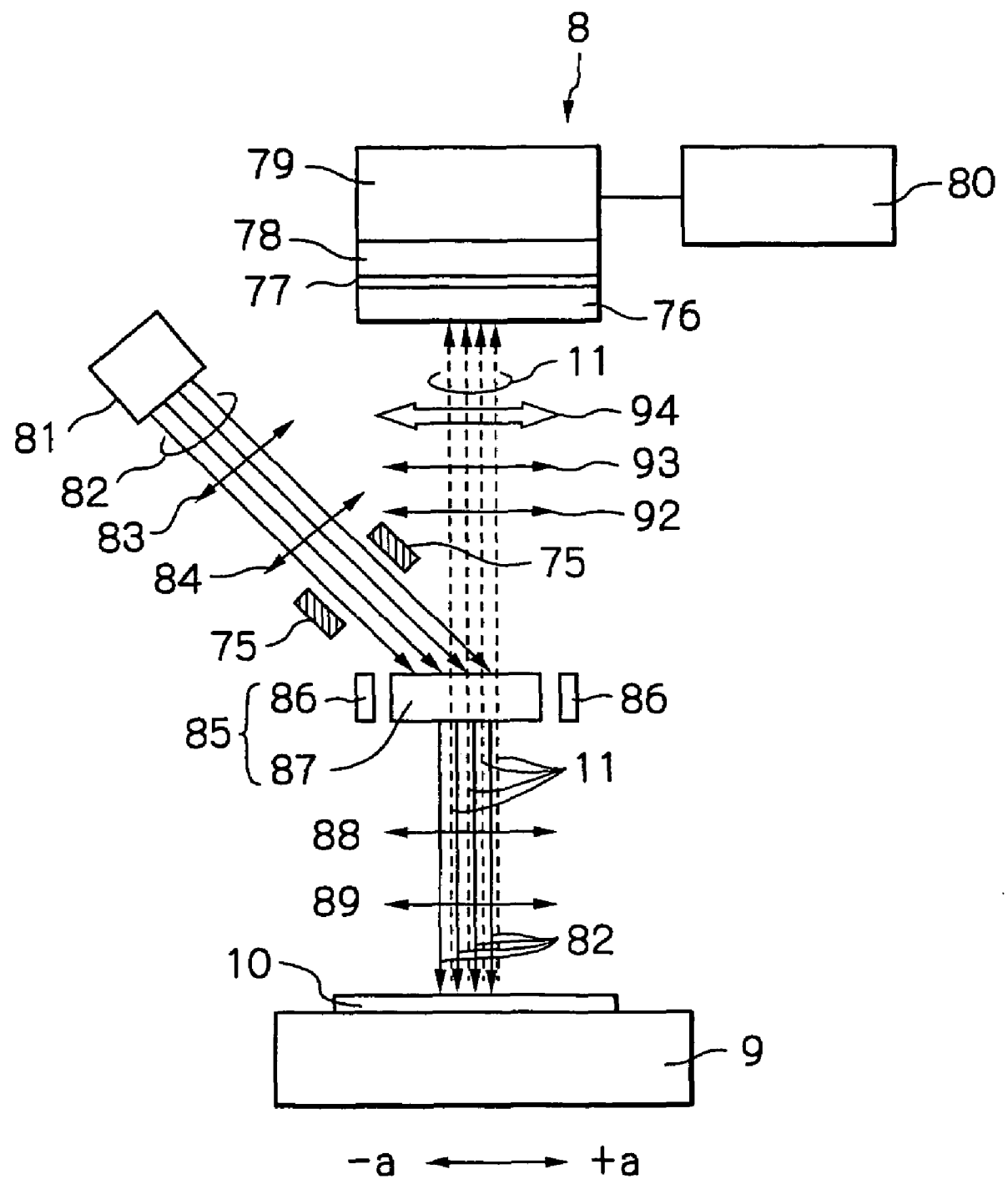
FIG. 8 is a schematic diagram of an electron beam detecting apparatus 8 of the present invention.

FIG. 8 is a schematic diagram of an electron beam detecting apparatus 8 of projection type according to another embodiment of the present invention. In the detecting apparatus 8 of FIG. 8, some members similar to those in the embodiment of FIG. 7 are designated by the same reference numerals and any duplicated explanations will be omitted. In the detecting apparatus 8 of FIG. 8, an electron gun 81 emits a plurality of primary electron beams 82. Thus emitted respective primary electron beams 82 pass though lenses 83 and 84 and then focused on a central area on a deflecting plane of an E×B deflector 85 (the Wien filter 85) composed of an electrode 86 and a magnet 87, each forming an elliptical image thereon. Specifically, each primary electron beam 82 is, for example, focused on the central area of the deflecting plane of the Wien filter 85 by the two-step of lenses 83 and 84 so as to form the elliptical image of 10 μm×12 μm, and also is operated by a deflector 75 to make a raster-scanning in the direction orthogonal to the drawing paper, so that the primary electron beams, as a whole, can cover uniformly a rectangular area of 1 mm×0.25 mm (the central area on the deflecting plane of the Wien filter 85).

Then, the primary electron beam is deflected by the Wien filter 85, demagnified by a lens 88 in a scale, for example, of ⅕, and irradiated generally vertically onto a sample 10 so as to cover a specific area of 200 μm×50 μm on the sample 10. At that time, the plurality of primary electron beams 82 is scanned by the deflector 75 all at once in the direction orthogonal to the drawing paper, while a stage 9 carrying the sample 10 thereon is serially moved in the +a (or −a) direction, whereby the electron beams, as a whole, are irradiated uniformly on the rectangular area on the surface of the sample 10.

It is to be noted that if the area subject to detection is quite large, then, when the primary beams 82 reach the end portion of the area on the sample 10 subject to detection in the "a" direction, the stage 9 is moved by steps in the direction of scanning (the direction orthogonal to the drawing paper) by a scanning width of the electron beams 82, and subsequently the stage 9 is serially moved in the −a (or +a) direction opposite to the direction of last movement. By repeating this movement of the stage 9 and the scanning operation of the primary electron beams 82 provided by the deflector 75, the specified area on the sample 10 subject to detection could be exposed to the uniform irradiation of the electron beams.

In the detecting apparatus of FIG. 8, the sample 10 emanates secondary electrons, back scattered electrons and reflected electrons 11 from respective irradiation points in response to the irradiation of the electron beams. The beam of the emanated secondary electrons or reflected electrons 11 are magnified by the lenses 89, 88, 92 and 93, and then a magnetic lens 94 makes the angle correction between the orientation of the light accepting plane of the TDI-CCD sensor 79 and the serial movement direction "a" of the sample 10. The beam of the secondary electrons, after having experienced the angle correction, is focused on a micro channel plate (MCP) 76 to form a rectangular image as a whole. These secondary electrons are increased in sensitivity by 10,000 to several 10,000 times by the MCP 76, converted into a light by a scintillator or a fluorescent section 77, and then pass through a relay optical system 78 into the TDI-CCD sensor 79, where the secondary electrons become electric signals in synchronization with the serial movement velocity of the sample and displayed as a series of images on an image display section 80.

The electron beam needs to be adjusted so as to be irradiated against the surface of the sample 10 as uniformly as possible with reduced uneven irradiation, for example, in a rectangular or elliptical shape of irradiation. Further, in order to improve the throughput, a large amount of irradiation current needs to be applied to the area of detection. This is because applying larger amount of irradiation current allows the moving velocity of the stage to increase correspondingly, thereby improving the throughput.

In the conventional detecting apparatus using a single electron beam, uneven irradiation may be counted to about ±10%, and disadvantageously, the high throughput is not feasible due to a current as low as 500 nA available for the irradiation of the electron beam. Further, in comparison with a scanning electron microscope (SEM), the electron beam apparatus of projection type is problematic in that more obstacles are apt to occur in imaging process due to the charge-up resultant from a block irradiation of the electron beam applied against an extended image observation area all at once.

In contrast, since in the detecting apparatus 8 of FIG. 8, the plurality of electron beams are used to scan and thus irradiate the sample, the unevenness in irradiation can be reduced, for example, to ⅓ as compared to the case of conventional electron beam apparatus. The amount of current used for irradiation as measured entirely over the sample surface, if using eight electron beams, could be 3 times greater than the case of the conventional system. As the number of electron beams used increases, consequently the throughput increases.

Though not shown in FIG. 8, the electron beam apparatus according to the present invention may comprise, in addition to the lenses, a variety of apertures, such as numerical apertures (NA) and field apertures, a deflecting systems (aligners)

including four or more poles for axial alignment of the electron beam, an stigmatism corrector (a stigmeter), and units required for illuminating and imaging operation for the electron beam including a plurality of quadrupole lenses (four-pole lenses) for modifying the beam shape.

Figure 11:
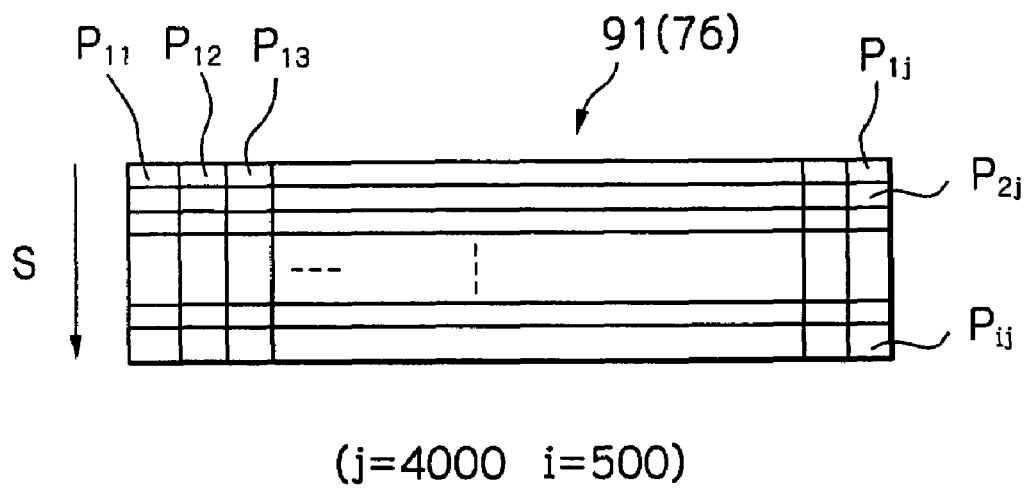
FIG. 11 is a plan view showing pixels P11 to Pij on the sensor surface 91 of an EB-TDI sensor 76.
Figure 12:
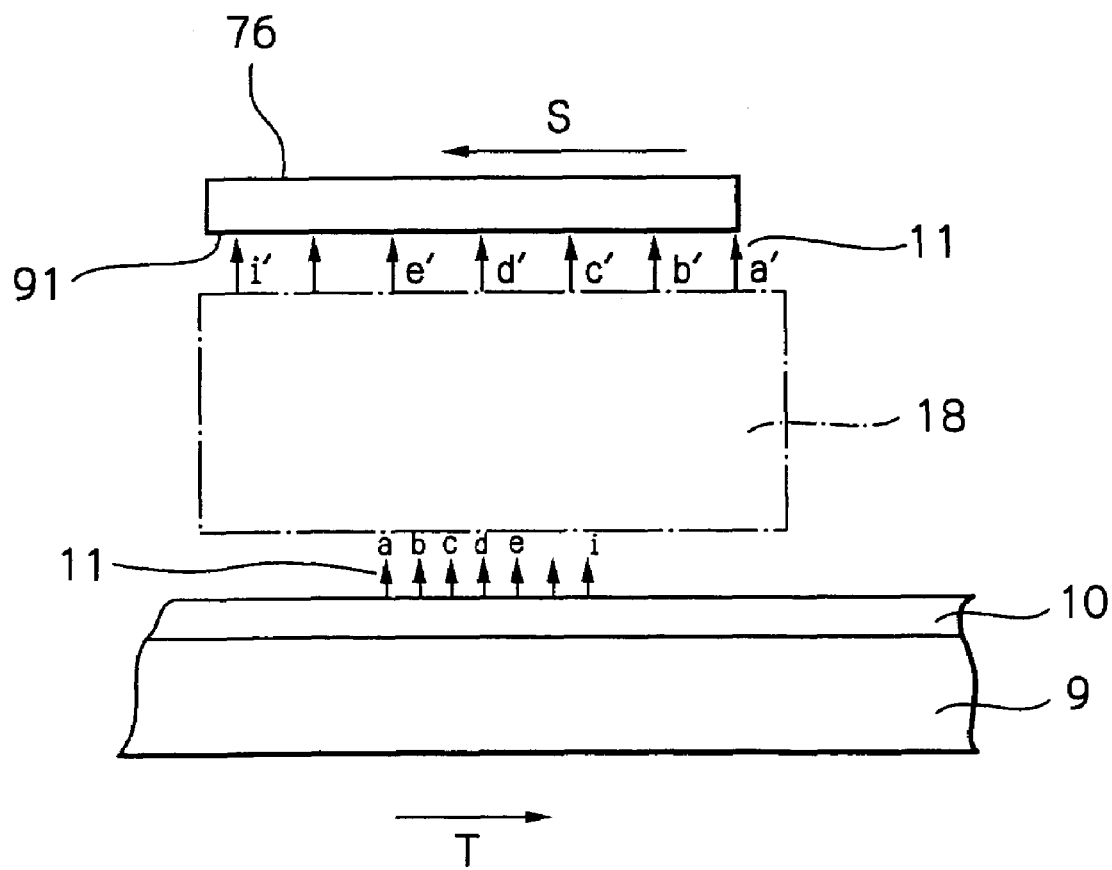
FIG. 12 is a schematic diagram illustrating a physical relationship between the EB-TDI sensor 76 and a secondary electron beam.

FIG. 11 is a plan view illustrating pixels P11 to Pij on the sensor surface 91 of the EB-TDI sensor 76. In FIG. 11, the arrow S indicates the direction of integration on the sensor surface 91. The pixels P11 to Pij of the sensor 76 has a configuration of 500 steps in the direction of integration (the number of integration steps i=500) and 4000 pieces in the direction normal to the direction of integration (j=4000). FIG. 12 is a schematic diagram illustrating a physical relationship between the EB-TDI sensor 76 and a secondary electron beam. In FIG. 12, the arrow S indicates the direction of integration on the sensor surface 91, and the arrow T indicates the direction of the continuous movement of the stage 9 carrying the wafer 10 thereon.

In FIG. 12, if the secondary-electron beam 11 from the wafer 10 is being emanated from the same location on the wafer 10 for a certain period of time, as the stage 9 moves in the direction indicated by the arrow S, the secondary electron beam 11 sequentially enters a series of locations a, b, c, d, e, . . . , i (i represents the number of integration steps) on the optical system 18 of map projection type in order of a→b→c→d→e . . . →i. The secondary electron beam 11, having once entered the optical system 18 of map projection type, is sequentially emitted from a series of locations a', b', c', d', e', . . . , i' on the optical system 18 of map projection type. At that time, if the movement for the charge integration of the EB-TDI sensor 76 in the direction of integration is synchronized with the movement of the stage 9, then the secondary electrons emitted from the locations a', b', c', d', e', . . . , i' of the optical system 18 of map projection type sequentially enter the same points on the sensor surface 91, thereby enabling the charges to be integrated by the number of integration steps i. In this way, respective pixels P11 to Pij on the sensor surface 91 can obtain more signals of the emitted electrons, thereby achieving the higher S/N ratio and allowing to obtain the two-dimensional (electronic) image at higher rate. The optical system 18 of map projection type has, for example, a scale factor of 300.

In the above explanation, a case of secondary electron beam which is one of secondary radiation beams emanated from the sample is taken, however, the other secondary radiation beam can also be dealt with in the same way.

In the embodiment shown in FIG. 8, the information processing section, which is not shown, may be arranged after the TDI-CCD sensor 79, so that the information processing section may use the image information obtained in the TDI-CCD sensor 79 to make a comparison among a plurality of cell images and/or a plurality of die images, thereby detecting defects on the surface of the sample and determining the features such as the shape, the position coordinates and the number of the detected defects, which may in turn be indicated on the image display section.

In another case where the surface structure of the oxide film or the nitride film of the semiconductor substrate prepared as the sample 10 is different from one another, or where the processing process is different from one another, an adequate condition for irradiation should be individually set for each different sample, and thus obtained images will be indicated on the image display section 80, from which the defects may be detected.

Figure 9:
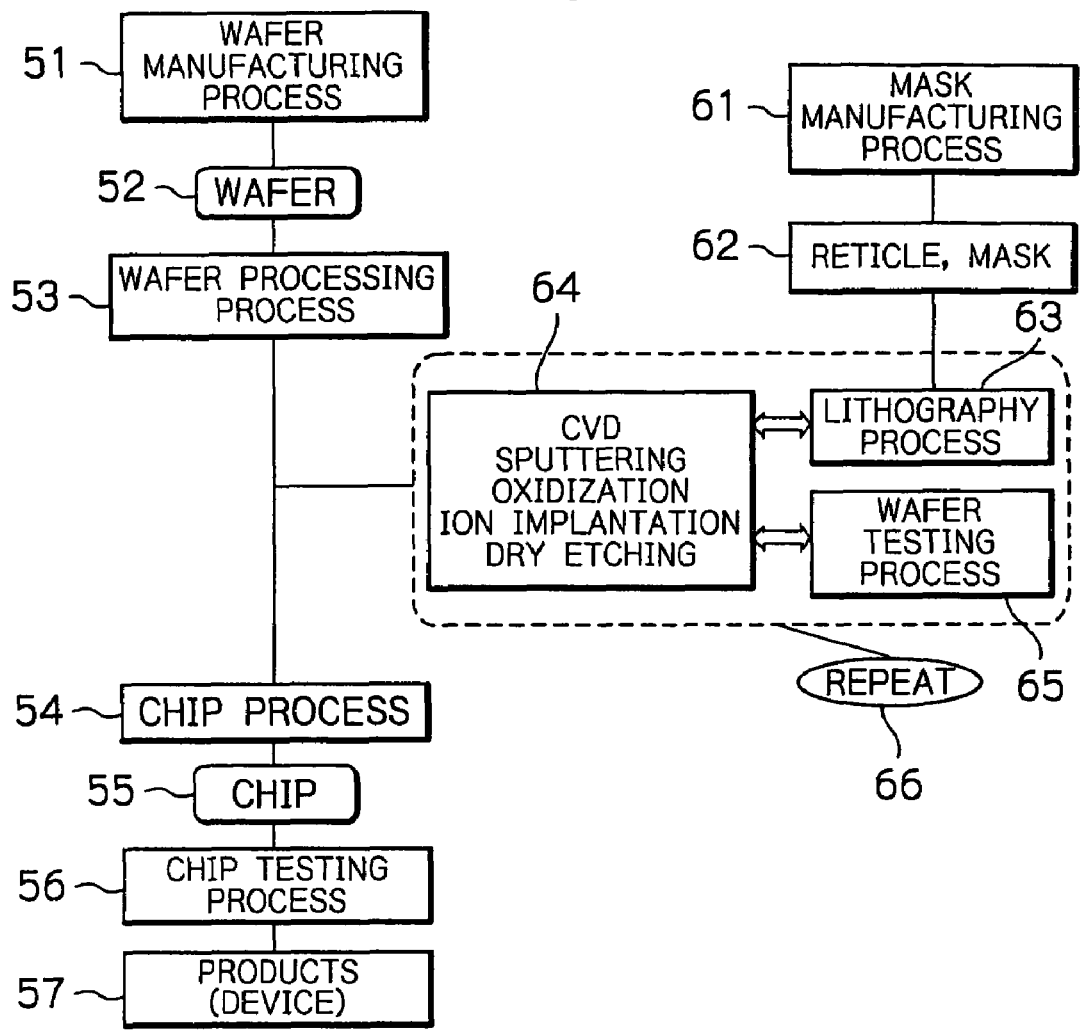
FIG. 9 is a flow chart illustrating an embodiment of a method of manufacturing a semiconductor device using an electron beam detecting apparatus or a detecting method, or a combination thereof according to the present invention.

FIG. 9 is a flow chart illustrating an embodiment of a method of manufacturing a semiconductor device using a electron beam detecting apparatus according to the present invention. The manufacturing processes shown in FIG. 9 include the following main processes:

(1) a wafer manufacturing process 51 for manufacturing a wafer 52 or a wafer preparing process for preparing a wafer 52;

(2) a mask manufacturing process 61 for manufacturing masks (reticles) 62 for use in exposure or mask preparing process for preparing masks;

(3) a wafer processing process 53 for performing the processing required to the wafer;

(4) a chip assembling process 54 for excising one by one chips 55 formed on the wafer and making them operable; and (5) a chip testing process 56 for testing complete chips and a process for obtaining products (semiconductor devices) which have passed the inspection.

The respective main processes are further comprised of several sub-processes. Right part of FIG. 9 shows sub-processes of the wafer processing process 53.

Among above main processes (1)-(5), the wafer processing process 53 set forth in (3) exerts critical affections to the performance of resulting semiconductor devices 57. This process involves sequentially laminating designed circuit patterns on the wafer to form a large number of chips which operate as memories, MPUs and so on. The wafer processing process includes the following sub-processes:

(6) a thin film forming sub-process 64 for forming dielectric thin films serving as insulating layers, metal thin films for forming wirings or electrodes, and so on (using CVD, sputtering and so on);

(7) an oxidization sub-process 64 for oxidizing the thin film layers and the wafer substrate;

(8) a lithography sub-process 63 for forming a resist pattern using masks (reticles) for selectively processing the thin film layers and the wafer substrate;

(9) an etching sub-process 64 for processing the thin film layers and the substrate in conformity to the resist pattern (using, for example, dry etching techniques);

(10) an ion/impurity injection/diffusion sub-process 64;

(11) a resist striping sub-process; and

(12) a sub-process for testing the processed wafer.

As will be appreciated, the wafer processing process 53 is repeated a number of times equal to the number of required layers to manufacture semiconductor devices which operate as designed.

The flow chart of FIG. 9 shows above mentioned processes (6), (9) and (10) together in a block 64, comprising an additional wafer testing process 65. Block 66 shows the processes repeated. To use the detecting apparatus according to the present invention in the sub-process for testing processed wafers in the above mentioned process (12), it is possible to test semiconductor devices having fine patterns with a high throughput, to test entire number of products, to increase yield rate of the products, and to prevent shipping of faulty products.

Figure 10:
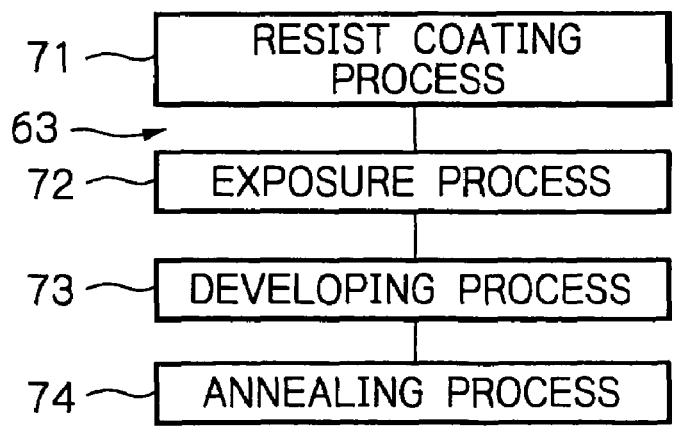
FIG. 10 is a flow chart illustrating the detail of the lithography process in the manufacturing method of FIG. 9.

FIG. 10 is a flow chart illustrating the detail of the lithography process 63 in the manufacturing method of FIG. 9. As shown in FIG. 10, the lithography process 63 includes the following steps:

(13) a resist coating step 71 for coating a resist on the wafer on which circuit patterns have been formed in the previous process;

(14) a step 72 of exposing the resist;

(15) a developing step for developing the exposed resist to produce a resist pattern; and

(16) an annealing step 74 for stabilizing the developed resist pattern.

Since the aforementioned semiconductor device manufacturing process, wafer processing process and lithography process are well known, and therefore no further description will be required.

EFFECT OF THE INVENTION

The detecting apparatus according to the present invention, in which secondary electrons emanated from the wafer are irradiated onto the sensor within the vacuum chamber, no longer requires an optical lens, an FOP, a hermetic glass or fittings for those components, thereby achieving a reduced number of components included in the detecting apparatus, an improved position accuracy and resolution, an elimination of the possible deterioration in the optical features transmitted to the sensor, and a lower cost of the apparatus. For example, advantageously, the present invention can improve the contrast by 2 to 4 times, reduce the cost of the detecting apparatus by 30 to 50%, improve the resolution by 1.5 to 3 times, and reduce the size of the detecting apparatus by about 50%. The use of the detecting apparatus according to the present invention can provide an inspection performance to a surface of a sample with a high resolution as well as a high throughput.

What is claimed is:

1. A detecting apparatus for detecting a defect on a surface of a sample, comprising:
    a radiation source for emitting an UV-ray or a Laser beam toward the sample held in a vacuum environment;
    an electron gun for emitting an irradiation beam toward the sample so that secondary electrons are emanated from the sample;
    an EB-CCD sensor for detecting the secondary electrons emanated from the sample, the EB-CCD sensor permitting the secondary electrons to enter the sensor surface directly to form a two dimensional image, said EB-CCD sensor being disposed in the vacuum environment;
    an electron-optical system for guiding the secondary electrons to the EB-CCD sensor; and
    a stage for mounting and moving the sample;
    wherein a processing device processes the image to detect a defect on the surface of the sample;
    a flange for separating the vacuum environment and the atmosphere, said flange including a feed through which has conductive pins connected directly to a camera in the atmosphere, a surface of the camera contacting with an outer surface of the flange around the feed through;
    a sensor package for integrating the EB-CCD sensor and signal transmission pins, the sensor package being installed in the vacuum environment;
    a connecting socket for connecting the conductive pins of the feed through and the signal transmission pins of the sensor package, said connecting socket including an elastic member for reducing a connecting pressure applied to said transmission pins.

2. A detecting apparatus according to claim 1, wherein said electron-optical system comprises symmetric tablet lenses between the sample and the sensor package.

3. A detecting apparatus for detecting a defect on a surface of a sample, comprising:
    an electron gun for emitting an irradiation beam toward the sample so that reflected electrons are emanated from the sample;
    an EB-CCD sensor for detecting the reflected electrons emanated from the sample, the EB-CCD sensor permitting the reflected electrons to enter the sensor surface directly to form a two dimensional image, said EB-CCD sensor being disposed in the vacuum environment;
    an electron-optical system for guiding the reflected electrons to the EB-CCD sensor;
    a stage for mounting and moving the sample;
    a processing device processing the image to detect a defect on the surface of the sample, and
    a flange for separating the vacuum environment and the atmosphere, said flange including a feed through which has conductive pins connected directly to a camera in the atmosphere, a surface of the camera contacting with an outer surface of the flange around the feed through;
    a sensor package for integrating the EB-CCD sensor and signal transmission pins, the sensor package being installed in the vacuum environment;
    a connecting socket for connecting the conductive pins of the feed through and the signal transmission pins of the sensor package, said connecting socket including an elastic member for reducing a connecting pressure applied to said transmission pins.

4. A detecting apparatus according to claim 3, wherein said electron-optical system comprises symmetric tablet lenses between the sample and the sensor package.

* * * * *